US00PP25459P2

(12) United States Plant Patent
Sakazaki

(10) Patent No.: US PP25,459 P2
(45) Date of Patent: Apr. 21, 2015

(54) ***PETUNIA* PLANT NAMED 'USTUN51501'**

(50) Latin Name: *Petunia×hybrida*
Varietal Denomination: USTUN51501

(71) Applicant: Ushio Sakazaki, Hikone (JP)

(72) Inventor: Ushio Sakazaki, Hikone (JP)

(73) Assignee: Plant 21 LLC, Bonsall, CA (US)

( * ) Notice: Subject to any disclaimer, the term of this patent is extended or adjusted under 35 U.S.C. 154(b) by 158 days.

(21) Appl. No.: 13/815,882

(22) Filed: Mar. 15, 2013

(51) Int. Cl.
*A01H 5/00* (2006.01)

(52) U.S. Cl.
USPC ..... Plt./356.18

(58) Field of Classification Search
USPC ..... Plt./356.18, 356.17, 356.2
See application file for complete search history.

*Primary Examiner* — Kent L Bell
(74) *Attorney, Agent, or Firm* — C. A. Whealy

(57) ABSTRACT

A new and distinct cultivar of *Petunia* plant named 'USTUN51501', characterized by its outwardly spreading to trailing and mounding plant habit; freely branching habit; vigorous growth habit; early and freely flowering habit; small light purple-colored flowers with dark purple-colored venation and throat; and good garden performance.

1 Drawing Sheet

Botanical designation: *Petunia×hybrida*.
Cultivar denomination: 'USTUN51501'.

BACKGROUND OF THE INVENTION

The present invention relates to a new and distinct cultivar of *Petunia* plant, botanically known as *Petunia×hybrida* and hereinafter referred to by the name 'USTUN51501'.

The new *Petunia* plant is a product of a planned breeding program conducted by the Inventor in Higashiomi, Shiga, Japan and Bonsall, Calif. The objective of the breeding program is to create new freely-branching and uniformly mounding *Petunia* plants with early and freely flowering habit, unique attractive flowers and good garden performance.

The new *Petunia* plant originated from a cross-pollination made by the Inventor on May 18, 2010 in Higashiomi, Shiga, Japan of *Petunia×hybrida* 'Piccee White', not patented, as the female, or seed, parent with a proprietary seedling selection of *Petunia×hybrida* identified as code number P415-01, not patented, as the male, or pollen, parent. The new *Petunia* plant was discovered and selected by the Inventor as a single flowering plant within the progeny of the stated cross-pollination in a controlled greenhouse environment in Bonsall, Calif. on May 13, 2011.

Asexual reproduction of the new *Petunia* plant by vegetative cuttings in a controlled greenhouse environment in Bonsall, Calif. since May 14, 2011 has shown that the unique features of this new *Petunia* plant are stable and reproduced true to type in successive generations.

SUMMARY OF THE INVENTION

Plants of the new *Petunia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'USTUN51501'. These characteristics in combination distinguish 'USTUN51501' as a new and distinct *Petunia* plant:

1. Outwardly spreading to trailing and mounding plant habit.
2. Freely branching habit.
3. Vigorous growth habit.
4. Early and freely flowering habit.
5. Small light purple-colored flowers with dark purple-colored venation and throat.
6. Good garden performance.

Plants of the new *Petunia* can be compared to plants of the female parent, 'Piccee White'. In side-by-side comparisons conducted in Bonsall, Calif., plants of the new *Petunia* differ primarily from plants of 'Piccee White' in the following characteristics:

1. Plants of the new *Petunia* are more vigorous and mounding than plants of 'Piccee White'.
2. Plants of the new *Petunia* and 'Piccee White' differ in flower color as plants of 'Piccee White' have white-colored flowers.

Plants of the new *Petunia* can be compared to plants of the male parent selection. In side-by-side comparisons conducted in Bonsall, Calif., plants of the new *Petunia* differ primarily from plants of the male parent selection in the following characteristics:

1. Plants of the new *Petunia* are more mounding than and not as spreading as plants of the male parent selection.
2. Plants of the new *Petunia* and the male parent selection differ in flower color as plants of the male parent selection have pink-colored flowers.

Plants of the new *Petunia* can be compared to plants of 'USTUN47601', disclosed in U.S. Plant Pat. No. 24,521. In side-by-side comparisons conducted in Bonsall, Calif., plants of the new *Petunia* differed primarily from plants of 'USTUN47601' in the following characteristics:

1. Plants of the new *Petunia* were more vigorous than plants of 'USTUN47601'.
2. Plants of the new *Petunia* were not as freely flowering as plants of 'USTUN47601'.

3. Plants of the new *Petunia* and 'USTUN47601' differed in flower color as plants of 'USTUN47601' had coral red-colored flowers.

Plants of the new *Petunia* can also be compared to plants of 'USTUN34803', disclosed in U.S. Plant Pat. No. 22,884. In side-by-side comparisons, plants of the new *Petunia* differed primarily from plants of 'USTUN34803' in the following characteristics:

1. Plants of the new *Petunia* were more mounding than plants of 'USTUN34803'.
2. Plants of the new *Petunia* had larger flowers than plants of 'USTUN34803'.
3. Plants of the new *Petunia* and 'USTUN34803' differed in flower color as plants of 'USTUN34803' had red purple-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'USTUN51501' grown in a container.

The photograph at the top of the sheet is a close-up view of typical flowers of 'USTUN51501'.

DETAILED BOTANICAL DESCRIPTION

The aforementioned photographs and following observations, measurements and values describe plants grown during the late autumn in 11.4-cm containers in an outdoor nursery in Bonsall, Calif. During the production of the plants, day temperatures ranged from 18° C. to 38° C., night temperatures ranged from 9° C. to 18° C. and light levels ranged from 7,000 to 10,000 foot-candles. Plants were pinched one time and were three months old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN51501'.

Parentage:

*Female, or seed, parent.*—*Petunia×hybrida* 'Piccee White', not patented.

*Male, or pollen, parent.*—Proprietary seedling selection of *Petunia×hybrida* identified as code number P415-01, not patented.

Propagation:

*Type.*—Terminal vegetative cuttings.

*Time to produce a rooted young plant, summer.*—About 15 days at temperatures ranging from 16° C. to 29° C.

*Time to produce a rooted young plant, winter.*—About 20 days at temperatures ranging from 16° C. to 21° C.

*Root description.*—Medium in thickness, fibrous; white in color.

*Rooting habit.*—Freely branching; medium density.

Plant description:

*Plant and growth habit.*—Outwardly spreading to trailing and mounding plant habit; freely branching habit with about nine primary lateral branches with multiple secondary lateral branches developing per plant; dense and bushy appearance; pinching enhances development of lateral branches; vigorous growth habit.

*Plant height.*—About 14.5 cm.

*Plant diameter* (*area of spread*).—About 32 cm by 40 cm.

*Lateral branches.*—Length: About 32 cm. Diameter: About 2 mm. Internode length: About 2.5 cm. Aspect: Initially upright then falling outwardly. Texture: Pubescent; minute. Color: Close to 146C.

Foliage description:

*Arrangement.*—Alternate before flowering; opposite after flowers develop; simple.

*Length.*—About 4.6 cm.

*Width.*—About 2.2 cm.

*Shape.*—Elliptical.

*Apex.*—Broadly acute.

*Base.*—Attenuate.

*Margin.*—Entire.

*Texture, upper and lower surfaces.*—Pubescent; glandular.

*Venation pattern.*—Pinnate, arcuate.

*Color.*—Developing leaves, upper surface: Close to 146A. Developing leaves, lower surface: Close to 146B. Fully expanded leaves, upper surface: Close to N137A; venation, close to 146B. Fully expanded leaves, lower surface: Close to 146A; venation, close to 147C.

*Petioles.*—Length: About 1 cm. Diameter: About 3 mm. Texture, upper and lower surfaces: Sparsely pubescent. Color, upper and lower surfaces: Close to 147C.

Flower description:

*Flower type and flowering habit.*—Single axillary salverform flowers; flowers face mostly upward to outwardly; freely flowering habit with about 13 to 16 flowers developing per lateral branch and about 150 flowers developing per plant.

*Natural flowering season.*—Long day responsive; long flowering period, plants flower from early spring until frost in the autumn, flowering continuous during this period; early flowering habit, plants begin flowering about six weeks after planting.

*Flower longevity on the plant.*—About three to four days; flowers persistent.

*Fragrance.*—None detected.

*Flower buds.*—Length: About 3 cm. Diameter: About 6 mm. Shape: Oblong. Color: Close to 196D.

*Flower diameter.*—About 3.6 cm.

*Flower depth* (*height*).—About 3.5 cm.

*Throat diameter, distal.*—About 9 mm.

*Tube length.*—About 2.5 cm.

*Tube diameter, proximal.*—About 3.5 mm.

*Petals.*—Quantity and arrangement: Five petals fused in a single salverform whorl. Petal lobe length (from throat): About 1.5 cm. Petal lobe width: About 1.6 cm. Petal lobe shape: Obovate. Petal lobe apex: Broadly acute. Petal lobe margin: Entire. Petal lobe texture, upper surface: Smooth, glabrous; velvety. Petal lobe texture, lower surface: Mostly smooth with scattered pubescence along the veins. Throat texture: Smooth, glabrous. Tube texture: Pubescent. Color: When opening, upper surface: Close to 76C. When opening, lower surface: Close to 85C to 85D. Fully opened, upper surface: Close to 77C; venation, close to N77A; color becoming closer to 84C with development.

Fully opened, lower surface: Close to 84C to 84D; venation, close to N77C. Flower throat (inside): Close to 79C; venation, close to N77A. Flower tube (outside): Towards the apex, close to 79D; towards the base, close to 79B; venation, close to N77C.

*Sepals*.—Quantity and arrangement: Five sepals fused in a single star-shaped whorl. Length: About 1.4 cm. Width: About 3 mm. Shape: Lanceolate. Apex: Rounded to slightly acute. Margin: Entire. Texture, upper and lower surfaces: Pubescent; minute. Color, upper surface: Close to 137A. Color, lower surface: Close to 146B.

*Peduncles*.—Length: About 1.7 cm. Width: About 1 mm. Angle: About 30° from the stem axis. Strength: Strong. Texture: Pubescent; minute. Color: Close to 144B.

*Reproductive organs*.—Stamens: Quantity per flower: Five. Filament length: About 1.5 cm. Filament color: Close to 196D. Anther length: About 2 mm. Anther shape: Oval. Anther color: Close to 94C. Pollen amount: Moderate. Pollen color: Close to 98D. Pistils: Quantity per flower: One. Pistil length: About 2.2 cm. Style length: About 1.6 cm. Style color: Close to 92C to 92D. Stigma shape: Round. Stigma color: Close to N187A. Ovary color: Close to 144C.

*Seeds and fruits*.—Seed and fruit development has not been observed on plants of the new *Petunia*.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'USTUN51501' as illustrated and described.

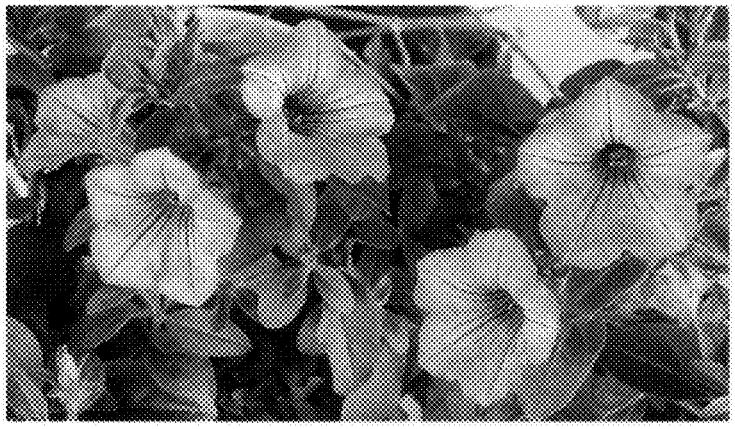
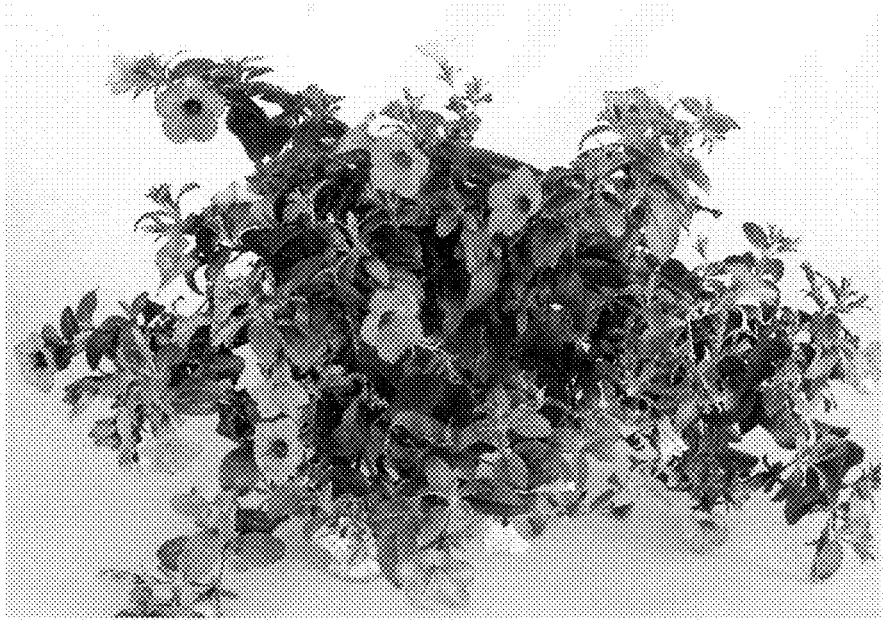

* * * * *